(12) United States Patent  
Hagen et al.

(10) Patent No.: US 8,702,852 B2  
(45) Date of Patent: Apr. 22, 2014

(54) CONDENSATION AND WASHING DEVICE, POLYMERISATION DEVICE AND METHOD FOR CLEANING PROCESS STEAM DURING THE PRODUCTION OF POLYLACTIDE

(71) Applicant: Uhde Inventa-Fischer GmbH, Berlin (DE)

(72) Inventors: Rainer Hagen, Berlin (DE); Udo Muhlbauer, Berlin (DE)

(73) Assignee: Uhde Inventa-Fischer GmbH (DE)

( * ) Notice: Subject to any disclaimer, the term of this patent is extended or adjusted under 35 U.S.C. 154(b) by 0 days.

(21) Appl. No.: 13/872,198

(22) Filed: Apr. 29, 2013

(65) Prior Publication Data

US 2013/0236366 A1 Sep. 12, 2013

Related U.S. Application Data

(62) Division of application No. 12/676,262, filed as application No. PCT/EP2008/006432 on Aug. 5, 2008, now Pat. No. 8,430,948.

(30) Foreign Application Priority Data

Sep. 3, 2007 (EP) .................................... 07017233

(51) Int. Cl.
*B01D 53/14* (2006.01)

(52) U.S. Cl.
USPC .................. 96/234; 95/211; 95/237; 528/486; 96/290

(58) Field of Classification Search
USPC ............. 134/31; 528/307, 354, 357; 549/274
See application file for complete search history.

(56) References Cited

U.S. PATENT DOCUMENTS

| | | | |
|---|---|---|---|
| 4,835,293 A | 5/1989 | Bhatia | |
| 5,266,706 A * | 11/1993 | Bhatia | 549/274 |
| 5,856,523 A | 1/1999 | Miao et al. | |
| 6,875,839 B2 | 4/2005 | Gerking et al. | |
| 7,781,600 B2 | 8/2010 | Ogawa et al. | |
| 8,430,948 B2 | 4/2013 | Hagen et al. | |
| 2001/0043898 A1* | 11/2001 | Stoltz et al. | 423/245.2 |
| 2010/0249364 A1 | 9/2010 | Hagen et al. | |
| 2010/0252076 A1 | 10/2010 | Hagen et al. | |

FOREIGN PATENT DOCUMENTS

| | | | |
|---|---|---|---|
| DE | 10257577 A1 | 7/2004 | |
| JP | 2007070413 A | 3/2007 | |
| WO | WO2006064611 A1 * | 6/2006 | C07C 51/43 |

OTHER PUBLICATIONS

U.S. Appl. No. 12/676,262, Ex Parte Quayle Action mailed Aug. 8, 2012, 5 pgs.
U.S. Appl. No. 12/676,262, Notice of Allowance mailed Jan. 3, 2013, 8 pgs.

(Continued)

*Primary Examiner* — Duane Smith
*Assistant Examiner* — Joubert X Glover
(74) *Attorney, Agent, or Firm* — Schwegman Lundberg & Woessner, P.A.

(57) ABSTRACT

The present invention relates to a condensation and washing device with which in particular the process vapors which occur during the production of polylactide can be processed and cleaned. Furthermore, the present invention relates to a polymerization device for the production of polylactide and also to a method for processing process vapors which occur during the production of polylactide; possibilities for use of both the condensation and washing devices and of the method are likewise mentioned.

21 Claims, 2 Drawing Sheets

(56) References Cited

OTHER PUBLICATIONS

Figure 1:
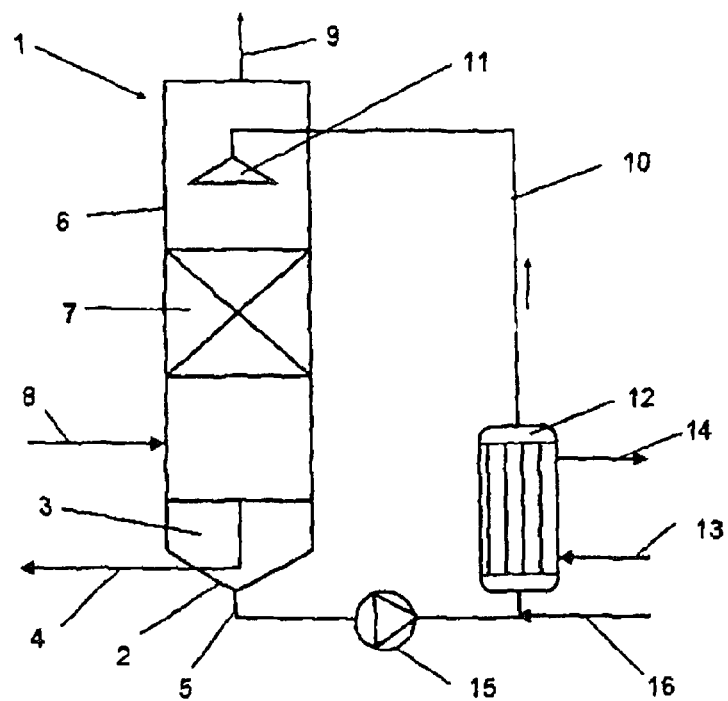

U.S. Appl. No. 12/676,262, Response filed Oct. 1, 2012 to the Ex Parte Quayle Action mailed Aug. 8, 2012, 11 pgs.
European Application No. 07017233.3, Search Report dated Jan. 30, 2008, 9 pgs.
International Application No. PCT/EP2008/006432, English Translation of International Preliminary Report on Patentability mailed Apr. 15, 2010, 11 pgs.
International Application No. PCT/EP2008/006432, International Search Report and Written Opinion, (Nov. 20, 2008), 16 pgs.

* cited by examiner

CONDENSATION AND WASHING DEVICE, POLYMERISATION DEVICE AND METHOD FOR CLEANING PROCESS STEAM DURING THE PRODUCTION OF POLYLACTIDE

PRIORITY CLAIM TO RELATED APPLICATIONS

This application is a divisional of and claims the benefit of priority to U.S. patent application Ser. No. 12/676,262, filed on Jun. 24, 2010, which is a U.S. national stage application under 35 U.S.C. §371 of PCT/EP2008/006432, filed Aug. 5, 2008, and published as WO 2009/030330 A1 on Mar. 12, 2009, which claims priority to European Application No. 07017233.3, filed Sep. 3, 2007, which applications and publication are incorporated herein by reference and made a part hereof in their entirety, and the benefit of priority is claimed thereto.

Embodiments of the present invention relate to a condensation and washing device with which in particular the process vapours which occur during the production of polylactide can be processed and cleaned. Furthermore, embodiments of the present invention relate to a polymerisation device for the production of polylactide and also to a method for processing process vapours which can occur during the production of polylactide; possibilities for use of both the condensation and washing devices and of the method are likewise mentioned.

The process steps for the production of polylactide concern for example direct polycondensation of lactic acid, thermal depolymerisation of polylactide into dilactide, cleaning of the dilactide by means of distillation, rectification or crystallisation, polymerisation and demonomerisation. The vapours from these process steps occur under reduced pressures or vacuum which can be between 5 mbar and 200 mbar. According to the process step, they contain water, lactic acid, dilactide and lactoyllactate in different compositions. These components can be condensed as far as possible for protection of the vacuum pumps but also for economic process reasons and be returned into the process.

The condensation of dilactide-containing vapours on cooled surfaces of condensers presents difficulties. An aerosol is produced which cannot be precipitated with normal means, such as drop or mist depositors, but leaves the condenser with the non-condensable residual gas and thus passes into the vacuum pumps which withdraw and condense this residual gas.

This problem is compounded inasmuch as the vapours from the process steps for the production of polylactide contain inert gases, such as air or nitrogen. In vacuum pumps, the dilactide aerosol leads within a short time, as a result of increased wear and tear of metallic surfaces, such as rotary pistons, rotary valves, rotary plungers and the housings thereof, to mechanical destruction. A further problem is the conversion of the dilactide by the water vapour which is always still contained in the residual gas into lactoyllactate which, together with the likewise still entrained lactic acid residues, attack these metallic surfaces by corrosion and permanently destroy them.

Indirect condensation on cooled surfaces is generally preferred since, in contrast to direct condensation with cold liquids, it introduces no additional substances, possibly extraneous, into the process and does not increase the quantity of condensate.

U.S. Pat. No. 5,266,706 describes a process for recovering a cyclic ester, such as lactide, from a gas flow which contains the lactide and hydroxyl group-containing impurities, such as water and hydroxycarboxylic acids, by washing the gas flow with a solvent which is not miscible with water, such as non-polar hydrocarbons, cylcoaliphatic hydrocarbons or halogenated hydrocarbons. The temperature is thereby adjusted during the washing such that the cyclic ester and the hydroxycarboxylic acid is removed from the gas flow, whilst water remains in the gas flow and is discharged with the latter. The crude mixture of cyclic ester and acid is separated from the solvent and cleaned in that the acid is extracted therefrom. However, it is disadvantageous with the mentioned process that the lactide which is cleaned in this manner contains, after the processing, process-foreign solvents, i.e. solvents which do not correspond to the educts contained in the original lactide flow and which must be removed again subsequent to the method by means of complex steps. This involves high complexity and costs.

Embodiments of the present invention can condense and wash process vapours from various steps in the production of polylactide so that vacuum pumps which produce the vacuum required in the individual process steps of the polylactide production are protected from accompanying substances which attack and destroy these pumps chemically (corrosion) or mechanically (abrasion). The condensation and washing liquid is thereby intended not to entrain any process-foreign substances into the condensate which would require to be separated again before recycling into the polylactide process.

This can be achieved with respect to the condensation and washing device, and the polymerisation device, with the method of the patent claims. The respective dependent claims thereby present advantageous developments. Possibilities for use both of the device and of the method are mentioned in the patent claims.

According to the invention, a condensation and washing device is hence provided, comprising a) a sump container, containing a condensation and washing liquid, the sump container having at least one inflow and at least one outflow,
b) applied thereon in a form fit, at least one column which has at least one mass transfer packing which fills the cross-section of the column at least partially, preferably entirely,
c) at least one supply line for process vapour which is disposed below the mass transfer packing of the column, and also
d) at least one discharge line for process vapour which is disposed above the mass transfer packing of the column, the outflow of the sump container being connected to the column in order to ensure circulation of the condensation and washing liquid via a pipeline and the inlet pipeline of the column being disposed above the mass transfer packing.

It is thereby preferred if the condensation and washing liquid contains an aqueous solution of an alpha-hydroxycarboxylic acid of formula I,

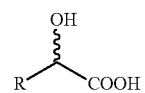

Formula I

R being selected from hydrogen or linear or branched aliphatic radicals with 1 to 6 carbon atoms, preferably lactic acid. The concentration of the alpha-hydroxycarboxylic acid (total acidity) is thereby in particular between 50 and 100% by weight, preferably between 70 and 95% by weight.

In addition, also a biodegradable, intermolecular cyclic diester of an alpha-hydroxycarboxylic acid of formula II,

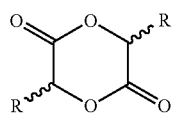

Formula II can be contained in the condensation and washing liquid which is in particular dilactide. Preferably, the concentration of the diester of formula II in the condensation and washing liquid is between 0 and 6% by weight, preferably between 1 and 4% by weight.

The mass transfer packing contained in the condensation and washing device thereby comprises in principle all the packing possibilities for columns known from the state of the art, however in particular the mass transfer packing is selected from the group comprising rings, such as e.g. Raschig and/or Pall rings, saddles, such as e.g. Berl saddle, spheres, hooks, NOR-PAC, BIO-NET, Hel-X, Top-Packs, Mellapak, Montz-Pak, Ralu-Pak, Raschig Super-Pak and/or packings made of fabric. The surface of the mass transfer packings used is thereby between $20 \text{ m}^2/\text{m}^3$ and $500 \text{ m}^2/\text{m}^3$.

In a further preferred embodiment, the at least one column has at least one liquid distributor for distributing the condensation and washing liquid which is supplied via the pipeline, said distributor being disposed above the at least one mass transfer packing. The liquid distributor is preferably a trickling or a spraying device, a spray condenser or a sprinkler.

In a further embodiment, the at least one column and/or the sump container have means for temperature control of the condensation and washing liquid. Additionally or alternatively hereto, it can likewise be provided preferably that the pipeline for the condensation liquid has a heat exchanger.

In order to remove the condensation and washing liquid which is enriched with the cyclic diester of formula II, it is preferred if a removal possibility for the condensation and washing liquid is present in the sump container. The removal can thereby be effected in portions or continuously.

Furthermore, a polymerisation device for polymerisation of the diester of formula II is provided according to the invention and comprises a previously described condensation device.

It is thereby advantageous if for example at least one cleaning device for dilactide which is operated under vacuum precedes the condensation device. It is likewise possible that at least one de-polymerisation reactor precedes the condensation device and is operated under vacuum.

According to the invention, a method is likewise provided for condensation and/or washing of a vaporous biodegradable, intermolecular cyclic diester of an alpha-hydroxycarboxylic acid of formula II

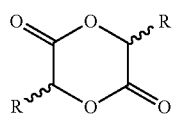

Formula II

R being selected from hydrogen or linear or branched aliphatic radicals with 1 to 6 carbon atoms,
comprising a vapour mixture, containing the diester of formula II, the alpha-hydroxycarboxylic acid of formula I corresponding to the diester of formula II, and water, a flow of a condensation and washing liquid containing an aqueous solution of the alpha-hydroxycarboxylic acid, corresponding to the diester of formula II, of formula I

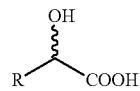

Formula I being brought into contact at least once with the vapour mixture, so that the diester of formula II, contained in the vapour mixture, is dissolved in the condensation and washing liquid. Bringing the vapour mixture into contact with the liquid can thereby be effected in any arbitrary manner. Thus it is possible for example that the vapour mixture is introduced into the condensation and washing liquid, for example by blowing in or conducting through, however, as an alternative hereto, it is also possible that the condensation and washing liquid is contacted by trickling, spraying or sprinkling of the vapour mixture.

It is thereby preferred if the condensation and washing liquid is conducted in a circulation.

Favourable temperature ranges of the condensation and washing liquid before being brought into contact with the vapour mixture are thereby between 10° C. and 80° C., preferably between 15° C. and 60° C.

In order to avoid the solubility limit of the diester of formula II in the condensation and washing liquid being exceeded, a mixture of water and hydroxycarboxylic acid of formula I is added to the condensation and washing liquid in portions or continuously. The quantity of aqueous solution of the hydroxycarboxylic acid of formula I which is to be added must thereby be measured such that it does not result in crystallising-out of the diester of formula II. Likewise, the added quantity should be measured in such a manner that the viscosity of the condensation and washing liquid remains approximately constant. The quantity or rate of the solution to be added hence depends upon various parameters, for example the temperature of the condensation and washing liquid and also the quantity of the diester of formula II in the vapour mixture so that the quantity or rate of the solution to be added in order to reduce the concentration of the diester of formula II in the washing and condensation liquid can be determined by the person skilled in the art in the respective case by means of simple experiments.

The concentration of the diester of formula II in the condensation and washing liquid is preferably always maintained below 5% by weight.

Furthermore, it is favourable if, after reaching a concentration of at most 5% by weight, preferably at most 3% by weight, of the diester of formula II in the condensation and washing liquid, an at least partial removal of the condensation and washing liquid is effected. The removal can thereby be effected likewise in portions or continuously.

A further preferred embodiment provides that the bringing into contact of the washing liquid with the vapour mixture is effected at reduced pressures, in particular between 5 mbar and 900 mbar, preferably between 10 mbar and 200 mbar.

Furthermore, it is advantageous if the diester of formula II is dilactide and the alpha-hydroxycarboxylic acid of formula I is lactic acid. The invention can be applied to both enantiomeric forms L,L-dilactide and D,D-dilactide and also L-lactic acid and D-lactic acid. Furthermore, it can be applied if the diester is D,L-dilactide or mesolactide.

Furthermore, it is possible that at least a part of the diester of formula II originates from a preceding cleaning device.

In the following, there is understood by dilactide L,L-dilactide, D,D-dilactide, mesolactide and also mixtures thereof.

The vapour mixture can likewise originate from different process steps during the polymerisation of lactide, namely from a process step for the production of polylactide, polycondensation of lactic acid, thermal depolymerisation of oligomers of lactic acid with an average molar mass between 500 g/mol and 5,000 g/mol, rectification of dilactide, ring-opening polymerisation of a dilactide-containing reaction mixture, vacuum-demonomerisation of polylactide or the copolymers thereof and/or from a plurality of the above-mentioned process steps at the same time.

In particular, the method described above can be implemented with a device likewise described above. Contacting of the vapour mixture with the washing or condensation liquid is thereby effected preferably in the region of the mass transfer packing.

Possibilities for use both of the device and the method are revealed in the production of biodegradable, intermolecular cyclic diesters of an alpha-hydroxycarboxylic acid of formula II, preferably dilactide, both L, L-dilactide and D,D-dilactide and D,L-dilactide (mesolactide), and also in the production of polymers from cyclic diesters of an alpha-hydroxycarboxylic acid of formula II, preferably polylactide (PLA), both L-polylactide (PLLA) and D-polylactide (DDLA) and D-L-polylactide (polymesolactide).

The method according to the invention is orientated towards obtaining not the cyclic ester—the lactide—but to cleaning the vapour flow of all condensable and abrasive or corrosive accompanying substances before it enters into a vacuum pump or a series of successively connected vacuum pumps. The temperature during the washing is chosen to be so low that, on the one hand, as large a proportion as possible of components contained in the vapour flow is condensed out, including water. On the other hand, it is chosen to be so high that the viscosity of the washing liquid is not too high so that good distribution over a packing layer or a mass transfer packing is still possible.

The method according to the invention does not operate with solvents which are extraneous to the process but essentially with the condensed-out liquid itself which is conducted in the circulation. The temperature of the washing liquid is thereby adjusted by the cooler disposed in the circulation and kept constant.

Surprisingly, it was now found that the direct condensation and washing of dilactide-containing vapour flows from process steps in the production of polylactide in packed beds or mass transfer packings which are sprayed with a cooled liquid, does not lead to formation of aerosols during the condensation. As cooling liquid, a mixture of water, lactic acid, linear oligomers of lactic acid and dilactide has proved to be suitable, which can be returned into the process of the polylactide production and there into a suitable process step and hence can be recovered. For the success of the aerosol-free condensation, the concentration of the mentioned components in the liquid mixture is not crucial. In principle, also a mixture of water and lactic acid is suitable for this purpose. It is however expedient to adjust the concentrations which, during stationary operation of the condenser and washer according to the invention, result under the prescribed vacuum and temperature of the condensation and washing liquid. Associated with stationary operation, on the one hand, is the discharge of a quantity of liquid from the circulation which corresponds to the quantity of condensate. On the other hand, dilactide-containing vapour flows which are condensed in the process according to the invention would lead to enrichment of the dilactide in the circulation of the condensation and washing liquid. This enrichment leads to the solubility limit of dilactide being exceeded and hence to precipitation of solids in the circulation liquid. This precipitation of solids effects blockages in the circulation and in particular in the packed bed or in the mass transfer packing. In addition, the dilactide reacts with the water contained in the liquid by ring-opening to form lactoyllactate. As a result, the viscosity of the liquid increases and the distribution over the bed or packing is made difficult and the condensation and washing effect is reduced. It is therefore advantageous to supply a mixture of water and lactic acid continuously or in portions to the condensation and washing liquid conducted in the circulation, the composition and flow quantity of which mixture is chosen such that the solubility limit of the dilactide in the circulation is not reached and the viscosity of the liquid mixture does not rise. A partial flow of the circulation liquid, corresponding to this rate of flow, is extracted in addition to the rate of flow of the condensate, preferably together with the latter, from the circulation, and is returned into the polylactide process at a suitable point.

The present invention is explained in more detail with reference to the accompanying Figures without however being restricted to the special embodiments illustrated there.

There are thereby shown

FIG. 1 a condensation device according to an embodiment of the invention, and

Figure 2:
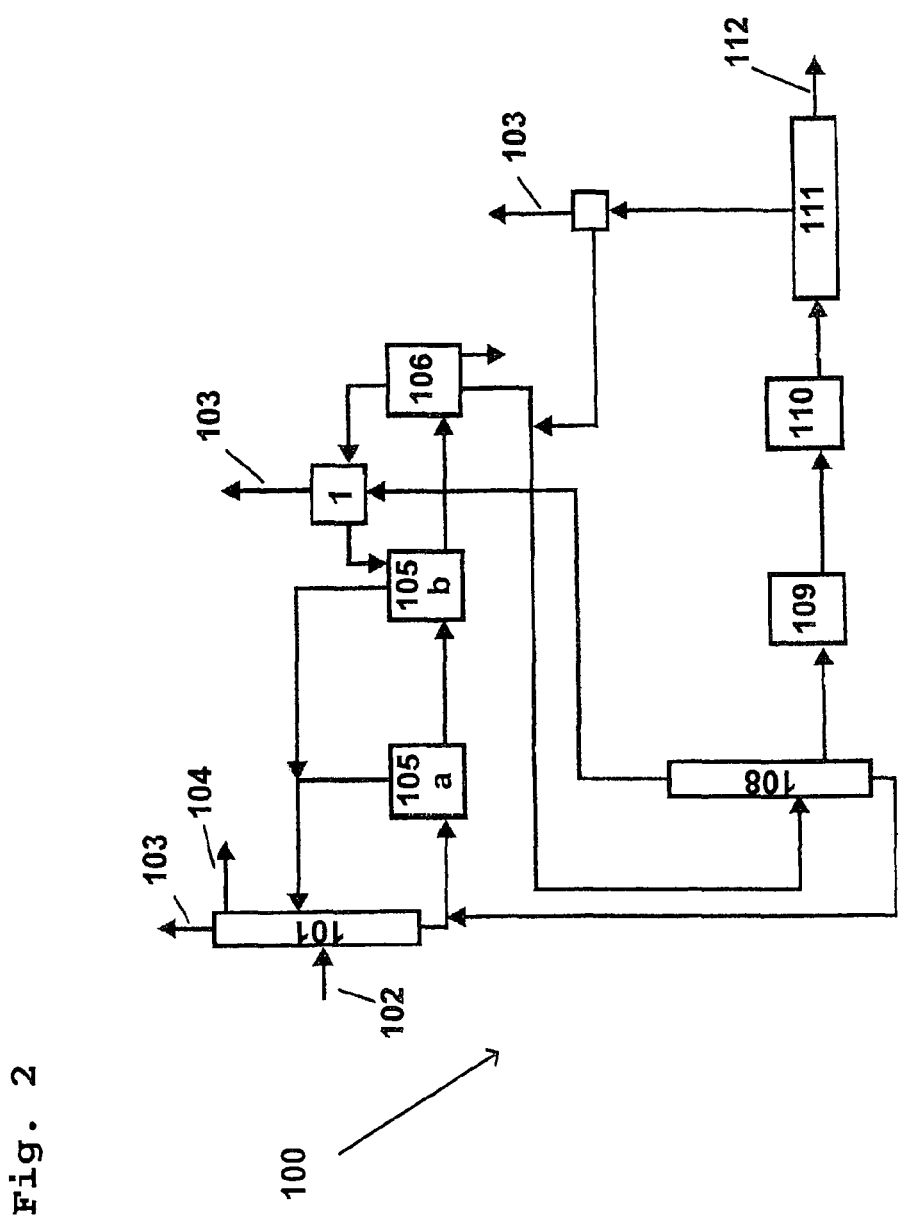

FIG. 2 an embodiment of a polymerisation device according to the invention with reference to a flow chart of a typical method implementation for the production of polylactide, starting from lactic acid.

A condensation device 1, the principle of which is shown in FIG. 1, contains a column unit 6 with a nominal diameter of 200 mm. In this unit, a packed bed 7 comprising Pall rings with the dimension 15 mm is disposed. The height of the packing is 500 mm. In the sump container 2, 60 l commercially available lactic acid (Purae HS88) are filled with a water content of 12% as condensation and washing liquid 3. The lactic acid is withdrawn from the sump by a pump 15, conveyed back through a heat exchanger 12 via a pipeline 10 into the column unit 6 and there is distributed uniformly over the packed bed 7 by means of a liquid distributor 11. For example, the liquid distributor 11 can be configured in the form of a sprinkler. The heat exchanger 12 controls the temperature of the liquid with a cooling medium 13 or 14, here ethylene glycol, to 30° C.

In the column unit 6, a pipe connection piece 9 is disposed above the packed bed 7 and the liquid distribution 11 and serves for discharging the non-condensable gasses and vapours. It is connected to a vacuum pump via a cooling trap (not shown in FIG. 1) which is cooled for example with dry ice to approx. −50° C.

The device 1 is set at a vacuum or reduced pressure of 10 mbar for dewatering. Thereafter, the sump is discharged as far as an overflow situated at the level of the outlet 4. The condensation device 1 is part of a continuous plant for the production of polylactide by means of ring-opening polymerisation. The above-described procedure is part of the start-up procedure of this plant. After the remaining process steps of the plant have also been set in operation, a vapour flow is supplied via connection piece 8 continuously to the condensation device 1, which vapour flow comes from the thermal depolymerisation of a lactic acid oligomer with an average molar mass $M_n$ of 1,500 g/mol and from which the main quantity of dilactide was already condensed out by a surface condenser. The vapour flow contains nitrogen, water, lactic acid and residual dilactide and has a temperature of 140° C. After entering into the condensation device 1, it flows, corresponding to the pressure gradient in the counter-flow, to the liquid 3 which is temperature controlled to 30° C. by the contact filter packing 7. A large part of the entrained components is thereby either condensed or washed out. The non-condensable residues, together with the contained nitrogen, leave the condensation device 1 through the gas outlet 9 and are deposited completely in the following cooling trap, the nitrogen being withdrawn by the vacuum pump.

In order to determine the rates of flow of the vapour and of the condensed and non-condensed proportions, the liquid level in the sump 2 is left to rise over 24 hours. Thereafter, the sump is emptied until the level before the beginning of the introduction of the vapour (overflow). The quantity of collected condensate is 5.9 kg, the water content is determined by Karl Fischer titration at 2% by weight. At the same time, the cooling trap in front of the vacuum pump is changed and the content weighed. 0.9 kg have been precipitated, the water content is determined at 90%. Dilactide could not be established by HPLC analysis. The vacuum pump shows no power loss which would imply wear or corrosion. If necessary, fresh aqueous lactic acid can be introduced into the circulation via the supply line 16.

In FIG. 2, the continuous overall process of the polylactide production (PLA process), starting from lactic acid, is illustrated. The process is subdivided thereby into the following partial steps which are implemented with the individual components which are integrated in the polymerisation device 100 and explained subsequently in more detail. The polymerisation device 100 thereby comprises a condensation device 1 according to the invention.

1. Concentration of Lactic Acid

The starting material for the process is lactic acid. The content of lactic acid must thereby be higher than 80% by weight. Preferably, the lactic acid concentration is thereby more than 90% because the water must be removed before polymerisation. The separation of water and lactic acid is thereby undertaken in a rectification column 101. A vacuum is thereby applied via a suction connection piece 103, the water present in vapour form is condensed and removed at the top via a further connection piece 104. The supply of the lactic acid is thereby effected continuously via a further connection piece 102. The distillate is pure water, the product occurring on the sump side is lactic acid with a concentration of more than 99% by weight.

In addition to separation of water from the original material (lactic acid), the rectification column 101 likewise serves for separation of the vapours from the precondensation reactors 105a and 105b. The vapour flows thereby comprise lactic acid, lactoyllactate, dilactide and water. The water is withdrawn at the top, lactic acid and derivatives thereof go into the sump of the rectification column and from there, together with the concentrated lactic acid, into the first precondensation reactor 105a.

2. Precondensation

The concentrated lactic acid is converted into a prepolymer in a series of two reactors 105a and 105b by polycondensation. The polycondensation takes place at two different pressures and temperatures in order to optimise the reaction conversion. In the first reactor 105a, the conditions are chosen such that the evaporation of lactic acid is minimised and the removal of water is facilitated at the same time. In the second step of the polycondensation, the reaction speed is increased by a higher temperature, the pressure is reduced at the same time in order further to reduce the water concentration in the melt. The average molar mass (number average) of the prepolymer is thereby between 500 and 2,000 g/mol.

3. Cyclising Depolymerisation

The prepolymer is in chemical equilibrium with the cyclic dimer of the lactic acid, the dilactide. By adjusting pressure and temperature in the depolymerisation reactor 106, it is ensured that the lactide is formed continuously from the prepolymer and evaporated. The vapour flow from the depolymerisation reactor 106 mainly comprises lactide. Water, lactic acid and the linear oligomers thereof are only present in subordinate quantities. The vapours are partially condensed in the condensation device 1 according to the invention: water and the largest proportion of lactic acid thereby remain in vapour form. The condensate first and foremost contains the lactide, lactoyllactate (the linear dimer of lactic acid) and higher linear oligomers. [Lactide is present in two stereoisomeric forms: the optically active L,L-lactide and the meso-lactide, made of a combination of an L(+)- and D(−)-lactic acid unit. The D(−)-units originate partly from the educt, partly they are formed by racemisation of L(+)-units during the prepolymerisation and the depolymerisation].

4. Lactide Cleaning

During the ring-opening polymerisation, the achievable molecular weight and hence significant mechanical properties of the polylactide depend upon the degree of purity of the lactide. The hydroxyl groups of the lactic acid and lactoyllactate contained as impurity thereby serve as the starting point of the polymerisation. The higher the concentration of the hydroxyl groups in the lactide, the less the achievable molecular weight of the polymer turns out to be. The concentration of the hydroxyl groups in the crude lactide is too high after the cyclising depolymerisation. The condensed lactide is cleaned in a rectification column or a membrane column 108 up to the required hydroxyl group concentration. The cleaned lactide is removed as by-product from the column 108. The distillate and the sump product are supplied again to the process at various places. In addition to the molecular weight of the polylactide, its properties are greatly influenced by the D-content (the quantity of structural units which have the D-configuration).

5. Ring-Opening Polymerisation

The ring-opening polymerisation is undertaken in a reactor which is formed from a combination of a stirred vessel 109 and a tubular reactor 110. In the first reactor 109, the low-viscous lactide is polymerised to form PLA with a conversion rate of approx. 50%. Catalyst and additives are mixed homogeneously into the melt.

In the tubular reactor 110, the polymerisation reaction is continued until a chemical equilibrium between polymer and monomer is reached. The maximum conversion of the monomer is approx. 95%. During polymerisation, the viscosity is increased to approx. 10,000 pa·sec.

6. Demonomerisation

In order to obtain a stable polylactide, the monomer concentration of approx. 5% by weight in the melt is too high. For this reason, demonomerisation must be implemented. This is achieved in a twin-screw extruder 111 by degassing the melt. On the basis of the fact that the ring-opening polymerisation is an equilibrium reaction, a stabiliser is added before the demonomerisation in order to prevent the re-formation of the monomer during and after the degassing.

7. Granulation and Crystallisation

Subsequent to the demonomerisation, the melt is removed from the extruder 111 and converted into a granulate 112. Both strand granulation or underwater granulation can thereby be implemented. In both cases, the PLA granulate must be crystallised before drying and packaging. The crystallisation is implemented at increased temperatures and with agitation until the granulate no longer adheres together.

A previously described condensation device 1 can be used for example for the purpose of separating dilactide vapours from the individual process steps in a process illustrated in FIG. 2. For this purpose, the condensation device is preferably used as integral component of an arrangement represented in FIG. 2. Supply of process vapours to the condensation device 1 can be effected from one, several or all process steps. Hence, the arrangement of the condensation device is not restricted to the arrangement illustrated in FIG. 2, the condensation device 1 can likewise follow and/or precede other process steps.

What is claimed is:

1. A condensation and washing device comprising:
    a) a sump container comprising a condensation and washing liquid and having at least one outflow, the condensation and washing liquid comprising an aqueous solution of an alpha-hydroxycarboxylic acid having formula I,

Formula I wherein R is chosen from hydrogen and linear or branched $C_{1-6}$ aliphatic radicals;
    b) at least one column on the sump container, the column comprising at least one mass transfer packing at least partially filling the cross-section of the column;
    c) at least one supply line to the column disposed below the mass transfer packing, the supply line comprising process vapour; and
    d) at least one discharge line from the column disposed above the mass transfer packing, the discharge line configured for process vapour;
    wherein the outflow of the sump container is fluidly connected to the column via a pipeline having an inlet to the column disposed above the mass transfer packing to circulate the condensation and washing liquid.

2. The condensation and washing device of claim 1, wherein the concentration of the alpha-hydroxycarboxylic acid is about 50 wt % to about 100 wt %.

3. The condensation and washing device of claim 1, wherein the concentration of the alpha-hydroxycarboxylic acid is about 70 wt % to about 95 wt %.

4. The condensation and washing device of claim 1, wherein the alpha-hydroxycarboxylic acid of formula I is lactic acid.

5. The condensation and washing device of claim 1, wherein the condensation and washing liquid comprises a biodegradable, intermolecular cyclic diester of an alpha-hydroxycarboxylic acid having formula II,

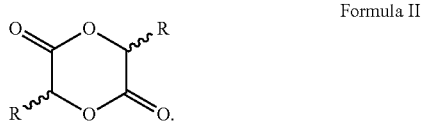

Formula II

6. The condensation and washing device of claim 5, wherein the biodegradable, intermolecular cyclic diester of an alpha-hydroxycarboxylic acid having formula II is dilactide.

7. The condensation and washing device of claim 5, wherein the concentration of the diester of formula II in the condensation and washing liquid is about 0 wt % to about 6 wt %.

8. The condensation and washing device of claim 5, wherein the concentration of the diester of formula II in the condensation and washing liquid is about 1 wt % to about 4 wt %.

9. The condensation and washing device of claim 1, wherein the mass transfer packing is chosen from rings, saddles, spheres, hooks, and packings comprising fabric.

10. The condensation and washing device of claim 1, wherein the mass transfer packing has a surface area of about $20\ m^2/m^3$ to about $500\ m^2/m^3$.

11. The condensation and washing device of claim 1, wherein the column comprises at least one liquid distributor disposed above the mass transfer packing, wherein the liquid distributor distributes the condensation and washing liquid supplied via the pipeline.

12. The condensation and washing device of claim 1, wherein at least one of the column and the sump container are configured to control the temperature of the condensation and washing liquid.

13. The condensation and washing device of claim 1, wherein the pipeline comprises a heat exchanger.

14. The condensation and washing device of claim 1, wherein the sump container comprises a removal line for the removal of the condensation and washing liquid.

15. A polymerisation device comprising at least one condensation and washing device of claim 1, wherein the polymerization device is for polymerisation of a biodegradable, intermolecular cyclic diester of an alpha-hydroxycarboxylic acid having formula II

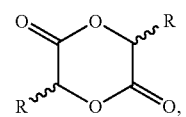

Formula II wherein R is chosen from hydrogen and linear or branched $C_{1-6}$ aliphatic radicals.

16. The polymerisation device of claim 15, wherein at least one cleaning device for the cyclic diester of formula II precedes the condensation and washing device.

17. The polymerisation device of claim 16, wherein at least one of a) the cleaning device comprises at least one membrane column and b) the cleaning device is operated under vacuum.

18. The polymerisation device of claim 15, wherein at least one depolymerisation reactor precedes the condensation device.

19. The polymerisation device of claim 15, comprising a polymerisation reactor, the polymerisation reactor comprising at least one stirred vessel and at least one tube reactor.

20. The condensation and washing device of claim 15, wherein the mass transfer packing is chosen from rings, saddles, spheres, hooks, and packings comprising fabric.

21. A condensation and washing device comprising:
    a) a sump container comprising a condensation and washing liquid and having at least one outflow, the condensation and washing liquid comprising an aqueous solution of an alpha-hydroxycarboxylic acid having formula I,

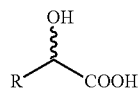

Formula I wherein R is chosen from hydrogen and linear or branched $C_{1-6}$ aliphatic radicals;
   b) at least one column on the sump container, the column comprising at least one mass transfer packing at least partially filling the cross-section of the column;
   c) at least one supply line to the column disposed below the mass transfer packing, the supply line comprising process vapour; and
   d) at least one discharge line from the column disposed above the mass transfer packing, the discharge line configured for process vapour;
   wherein the outflow of the sump container is fluidly connected to the column via a pipeline having an inlet to the column disposed above the mass transfer packing to circulate the condensation and washing liquid, and wherein the mass transfer packing is chosen from rings, saddles, spheres, hooks, and packings comprising fabric.

* * * * *